(12) United States Patent
Chen

(10) Patent No.: US 9,956,165 B2
(45) Date of Patent: May 1, 2018

(54) CONCENTRATED PROTEIN FORMULATIONS AND USES THEREOF

(75) Inventor: Tracy T. Chen, Katonah, NY (US)

(73) Assignee: CytoDyn Inc., Vancouver, WA (US)

( * ) Notice: Subject to any disclaimer, the term of this patent is extended or adjusted under 35 U.S.C. 154(b) by 660 days.

(21) Appl. No.: 13/582,243

(22) PCT Filed: Mar. 1, 2011

(86) PCT No.: PCT/US2011/026647
§ 371 (c)(1),
(2), (4) Date: Jan. 2, 2013

(87) PCT Pub. No.: WO2011/109365
PCT Pub. Date: Sep. 9, 2011

(65) Prior Publication Data
US 2013/0216525 A1    Aug. 22, 2013

Related U.S. Application Data

(60) Provisional application No. 61/339,191, filed on Mar. 1, 2010.

(51) Int. Cl.
| | |
|---|---|
| *A61K 39/395* | (2006.01) |
| *A61K 9/00* | (2006.01) |
| *A61K 47/18* | (2017.01) |
| *A61K 47/26* | (2006.01) |
| *C07K 16/00* | (2006.01) |

(52) U.S. Cl.
CPC ........ *A61K 9/0019* (2013.01); *A61K 39/3955* (2013.01); *A61K 47/183* (2013.01); *A61K 47/26* (2013.01); *C07K 16/00* (2013.01)

(58) Field of Classification Search
None
See application file for complete search history.

(56) References Cited

U.S. PATENT DOCUMENTS

| | | | |
|---|---|---|---|
| 7,390,786 B2 | 6/2008 | Warne et al. | |
| 7,648,702 B2 | 1/2010 | Gombotz et al. | |
| 7,666,413 B2 | 2/2010 | Liu et al. | |
| 7,705,132 B2 | 4/2010 | Rehder et al. | |
| 2003/0138417 A1* | 7/2003 | Kaisheva | A61K 9/0019 424/130.1 |
| 2003/0228306 A1* | 12/2003 | Olson | C07K 16/2866 424/143.1 |
| 2004/0197324 A1 | 10/2004 | Liu et al. | |
| 2006/0159653 A1 | 7/2006 | Saito et al. | |
| 2007/0065437 A1 | 3/2007 | Elson et al. | |
| 2007/0213270 A1 | 9/2007 | Costantino et al. | |

FOREIGN PATENT DOCUMENTS

| | | |
|---|---|---|
| EP | 1475100 | 11/2004 |
| JP | 2006-508631 A | 3/2006 |
| JP | 2007-217430 A | 8/2007 |
| JP | 2009-521482 A | 6/2009 |
| WO | 97/04801 A1 | 2/1997 |
| WO | 2003072766 | 9/2003 |
| WO | 2004/075913 A1 | 9/2004 |
| WO | WO 2005/112893 | 12/2005 |
| WO | 2007053533 | 5/2007 |

OTHER PUBLICATIONS

Pang Zhanjun et al., Analysis of Free Radical Medicine, pp. 331-332, 2000.
Castor et al., "The role of chemokines in mediating graft versus host disease: opportunities for novel therapeutics," *Front. Pharm.* 3:1-13, 2012.
Gilliam et al., "Clinical use of CCR5 inhibitors in HIV and beyond," *J. Trans. Med.* 9(Suppl. 1): S9, 2010. (14 pages).
Reshef et al., "Blockade of Lymphocyte Chemotaxis in Visceral Graft-versus-Host Disease," *N. Engl. J. Med* 367:135-145, 2012.
Yuan et al., "Prophylaxis of acute graft-versus-host disease by CCR5 blockade combined with cyclosporine A in murine model," *Inflamm. Res.* 64:137-144, 2015.

* cited by examiner

*Primary Examiner* — Yunsoo Kim
(74) *Attorney, Agent, or Firm* — SEED IP Law Group LLP

(57) ABSTRACT

Described are low viscosity, hypotonic formulations containing one or more proteins, e.g., antibodies, at high concentration, uses of the formulations, and articles of manufacture. In particular, the formulations are useful and beneficial for the subcutaneous administration or delivery of a high concentration of a protein drug, such as an antibody, to a subject who is afflicted with a disease or condition that is treatable by the protein drug.

21 Claims, No Drawings

CONCENTRATED PROTEIN FORMULATIONS AND USES THEREOF

RELATED APPLICATIONS

This application is a national stage filing under 35 U.S.C. § 371 of international PCT application, PCT/US2011/026647, filed Mar. 1, 2011, which claims the benefit under 35 U.S.C. § 119 of U.S. provisional application 61/339,191, filed Mar. 1, 2010, the entire contents of which are incorporated herein by reference.

TECHNICAL FIELD

The present disclosure is directed to stable protein formulations, specifically, formulations of a concentrated protein and methods of use thereof.

BACKGROUND

The development of concentrated protein formulations comprising proteins at a concentration of greater than 100 mg/mL presents many challenges. At such high concentrations, these proteins are restricted by solubility, administration volume and manufacturing limitations, stability issues, and delivery obstacles exist. Developing formulations in which the component protein is at present in high concentration may also present aggregation problems. Concentrated protein formulations specific for injectable administration present a particular complication in that they tend to be highly viscous. Not only do these formulations present potential difficulties during subcutaneous administration to an individual, but also during preparation and manufacture.

There is a need for highly concentrated protein formulations having low viscosity, particularly for the ready administration of protein-based drugs and biologics to subjects via parenteral routes. The present invention provides a solution to this need.

SUMMARY

In one of its aspects, the present invention provides a low viscosity, concentrated protein formulation, composition, or preparation which is hypotonic and can be readily administered to a subject, including humans, and readily manufactured and stored.

1) The invention further encompasses a formulation comprising a concentrated protein, a tonicifier comprising a salt and a buffer present in a combined amount of from about 110 mM to about 120 mM and a surfactant, wherein the formulation is hypotonic. In an embodiment, the concentrated protein is in an amount greater than about or equal to 100 mg/mL and less than about or equal to 200 mg/mL or in an amount of about 162 mg/mL to about 175 mg/mL. In an embodiment, the concentrated protein is an enzyme, a polypeptide, a peptide, an antibody or a fragment of an antibody, a monoclonal antibody, a polyclonal antibody, a nanobody, or a hybrid antibody. In an embodiment, the concentrated protein is a monoclonal antibody that is humanized or a fragment of the humanized antibody.

2) Formulations of the invention comprise a salt in an amount of less than 100 mM or in an amount that is about 90 mM, about 95 mM, equal to 90 mM, or equal to 95 mM. The salt may be one or more of ammonium chloride, ammonium sulfate, ammonium thiocyanate, arginine hydrochloride, calcium chloride, magnesium chloride, sodium acetate, sodium chloride, sodium gluconate, sodium lactate, sodium thiocyanate, zinc chloride, or any combination thereof. The buffer in the formulations is present in an amount of about or equal to 5 mM to about or equal to 25 mM, or about or equal to 5 mM to about or equal to 20 mM and may comprise one or more amino acids, or a derivative or L-molecular form thereof. The one or more amino acids may be histidine, glycine, or a combination of histidine and glycine. Other suitable buffer reagents include tartaric acid, maleic acid, succinic acid, citric acid and acetate acid.

3) The formulations may contain a surfactant, which is present in an amount of about or equal to 0.001% w/v to about or equal to 0.2% w/v, in an amount of about or equal to 0.005% to about or equal to 0.2%, or in an amount of about or equal to 0.05% to about or equal to 0.2%. The surfactant may be a detergent, pluronic, polysorbate, polysorbate 20 (e.g., Tween®20), polyethylene glycol, or a combination thereof.

4) The formulations may further contain a stabilizing agent, which may be in an amount from about or equal to 0.05% w/v to about or equal to 1.8% w/v, or from about or equal to 0.2% to about or equal to 1.8% w/v, or from about or equal to 0.3% to about or equal to 1.5% w/v of the total formulation. The stabilizing agent may be a monosaccharide, a disaccharide, or a combination thereof. The stabilizing agent may also be a sugar, a sugar alcohol, or a derivative thereof.

5) The formulations have a viscosity of about 25 cps to about 60 cps, or a viscosity of about 40 cps to about 50 cps. The formulations have a pH of from about 5.4 to about 6.4, or a pH of from about 5.4 to about 6, or a pH of 5.4 to 5.6. The formulations have an osmolality of less than about 290 mOs/kg, or an osmolality of about 250 mOs/kg to about 280 mOs/kg, or an osmolality of about 260 mOs/kg.

6) The formulations of the invention may comprise a therapeutic protein, such as any type of antibody, or a fragment thereof, for administration to a subject in need thereof. In an embodiment, the formulation is a liquid or solution formulation.

7) The invention further encompasses a liquid or solution formulation that includes a concentrated protein in an amount greater than or equal to 100 mg/mL and less than or equal to 200 mg/mL; a salt in an amount greater than or equal to 90 mM or 95 mM and less than or equal to 100 mM; a buffer in an amount greater than or equal to 5 mM and less than or equal to 25 mM; a surfactant in an amount greater than or equal to 0.001% w/v and less than or equal to 0.2% w/v; and, optionally, a stabilizing agent in an amount of about 0.05% w/v to about 1.8% w/v; wherein the formulation has an osmolality of about 250 to about 280 mOsm; a viscosity of about 25 cP to about 60 cP, a pH of from 5.4 to 6.4 and an osmolality of about 240 mOs/kg to about 280 mOs/kg.

8) The invention further encompasses a low viscosity, hypotonic, liquid formulation, which includes a concentrated protein in an amount greater than about or equal to 100 mg/mL and less than about or equal to 200 mg/mL, wherein the concentrated protein is any type of antibody, or a fragment thereof; a salt in an amount of about or equal to 90 mM or 95 mM; a buffer in an amount of about or equal to 20 mM; a surfactant in an amount of about 0.005% w/v; and optionally a stabilizing agent in an amount of about 0.05%-0.5% w/v.

9) The invention further encompasses a low viscosity hypotonic formulation, which includes a concentrated antibody or fragment thereof in an amount greater than about or equal to 100 mg/mL and less than about or equal to 200 mg/mL; a salt in an amount of about 90 mM or 95 mM, wherein the salt is sodium chloride; a buffer in an amount of about 20 mM, wherein the buffer is histidine; a surfactant in an amount of about 0.005% w/v, wherein the surfactant is polysorbate; and a stabilizing agent in an amount of about 0.3% w/v or about 0.6% w/v, wherein the stabilizing agent is sorbitol or sucrose, respectively. The formulation may be a liquid or solution formulation.

10) The invention further encompasses a low viscosity hypotonic formulation, which includes a concentrated antibody or fragment thereof in an amount greater than about or equal to 100 mg/mL and less than about or equal to 200 mg/mL; a salt in an amount of about or equal to 95 mM, wherein the salt is sodium chloride; a buffer in an amount of about or equal to 20 mM, wherein the buffer is a combination of glycine and histidine; and a surfactant in an amount of about or equal to 0.005% w/v, wherein the surfactant is a polysorbate. The formulation may further include a stabilizing agent in an amount of about 0.001% to 1.5% w/v, wherein the stabilizing agent is sorbitol or sucrose.

The invention further embraces an article of manufacture, which includes a container and a formulation comprising a protein in a concentration of greater than 100 mg/mL and less than 200 mg/mL, a tonicifier of a salt and a buffer present in an amount of from about 110 mM to about 120 mM, a surfactant and instructions for use. In an embodiment, the formulation in the article of manufacture further comprises a stabilizing agent in an amount of about 0.001% to 1.5% w/v. In an embodiment, the container is selected from a bottle, a vial, a syringe, a pen, a pump, a multidose needle syringe, a multidose pen, a jet injector, a syrette, an autoinjector, a pre-filled syringe, or a combination thereof. In an embodiment, the formulation is included in the container of the article of manufacture.

These and other aspects of the present disclosure will become apparent to those skilled in the art after a reading of the following detailed description, including the illustrative embodiments and examples.

DETAILED DESCRIPTION OF THE EMBODIMENTS

The present invention is directed to stable, low viscosity formulations, compositions, or preparations, which are hypotonic and comprise one or more proteins present in a high concentration, i.e. greater than 100 mg/mL and less than 200 mg/mL. The formulations, compositions, or preparations of the invention are useful in the delivery of a therapeutic or prophylactic medicament, biologic, drug, and the like, to a subject in need thereof. Throughout this disclosure, the terms formulation, composition and preparation are used interchangeably.

More specifically, the stable formulations containing a highly concentrated protein have a low viscosity, which is beneficial for parenteral and subcutaneous administration. In an embodiment, the formulation is pharmaceutically and/or physiologically acceptable and provides a stable vehicle for a protein that is in high concentration. The formulations may be presented in a kit or article of manufacture for commercial distribution and use.

It is noted that the percent amounts of components of the formulations described herein are present in w/v of the total formulation.

In one embodiment, a formulation of the invention comprises a protein in an amount greater than about 100 mg/ml to about 200 mg/ml; a salt in an amount less than about 100 mM, from about 50 mM to about 90 mM, from about 50 mM to about 95 mM, about or equal to 90 mM, or about or equal to 95 mM, a buffer in an amount of from about or equal to 5 mM to about or equal to 20 mM; less than about 20 mM, or equal to 20 mM; and a surfactant in an amount of about 0.001% to about 0.2%. In an embodiment, the formulation is hypotonic. In an embodiment, the formulation has low viscosity. In an embodiment, the formulation is in the form of a liquid or solution. In some embodiments, the formulation also comprises, in addition to a salt as a first tonicifier, a second non-salt tonicifying agent, such as a sugar, sugar alcohol, a monosaccharide, a disaccharide, or a combination thereof, such, that the osmolality of the formulation is less than about 290 mOs/kg, or about 260 mOs/kg.

In another embodiment, a formulation of the invention comprises a concentrated protein, or a high concentration of protein, in an amount of greater than about 100 mg/mL to about 200 mg/mL; a salt and a buffer present in combination in an amount of about 100 mM to about 120 mM, about 100 mM to about 115 mM, about 100 mM to about 110 mM, about or equal to 100 mM, about or equal to 110 mM, or about or equal to 115 mM; and a surfactant in an amount of about 0.001% to about 0.2%, or about 0.005% to about 0.2%, or about 0.05% to about 0.02%. In an embodiment, the formulation is hypotonic. In an embodiment, the formulation has low viscosity. In an embodiment, the formulation further comprises a sugar, sugar alcohol, a monosaccharide, a disaccharide, or a combination thereof. In an embodiment, the formulation is in the form of a liquid or solution. In an embodiment, the salt and, optionally, the sugar, sugar alcohol, mono- and/or di-saccharide function as one or more stabilizing agents or tonicifying agents in the formulation.

In another embodiment, a formulation of the invention comprises a concentrated protein in an amount greater than about or equal to 100 mg/mL and less than about or equal to 200 mg/mL, where the concentrated protein is any desired protein, such as, but not limited to, an antibody or a fragment thereof, a blood clotting factor, an enzyme, a peptide, a polypeptide, or combinations thereof; a salt in an amount of greater than or equal to 90 mM but less than 100 mM, or greater than or equal to 95 mM but less than 100 mM, wherein the salt is, for example, sodium chloride, sodium gluconate, sodium lactate, or combinations thereof; a buffer in an amount of about 5 mM to about 20 mM; about or equal to 20 mM, or about or equal to 25 mM, wherein the buffer is, for example, an amino acid such as glycine, histidine, or a combination thereof, or an organic acid such as succinic acid, maleic acid, tartaric acid, citric acid, or acetic acid, or a combination thereof; and a surfactant in an amount of about 0.001% to about 0.2% or about 0.005% to about 0.2%, for example, a nonionic detergent, polysorbate, and the like, or a combination thereof. The formulation may further comprise a sugar, a sugar alcohol, a monosaccharide, a disaccharide, or a combination thereof, in an amount of greater than about or equal to 0.05% w/v and less than about or equal to 1.6% w/v or 1.8% w/v, or in an amount sufficient to provide an osmolality of the formulation of about 260-280 mOs/kg, wherein nonlimiting examples include sorbitol, mannitol, sucrose, trehalose, glycerol, maltose, or lactose, or a combination thereof. In an embodiment, the protein is present in an amount greater than 100 mg/mL and less than 200 mg/mL. In an embodiment, the protein is present in an amount greater than or equal to 100 mg/mL and less than or equal to 180 mg/mL. In an embodiment, the protein is present in an amount greater than or equal to 100 mg/mL and less than or equal to 175 mg/mL.

In a further embodiment, a formulation of the invention comprises a concentrated protein in an amount greater than about or equal to 100 mg/mL and less than about or equal to 200 mg/mL, where the concentrated protein is an antibody; a salt in an amount of about 90 mM or about 95 mM, where the salt is sodium chloride; a buffer in an amount of about 20 mM, where the buffer is glycine and/or other forms of glycine; a surfactant in an amount of about 0.001%-0.2% w/v, where the surfactant is a polysorbate or Pluronic; and, optionally, a mono- or disaccharide in an amount of about 0.3% w/v to about 1.5% w/v. In an embodiment, the protein is present in an amount greater than about or equal to 100 mg/mL and less than about or equal to 180 mg/mL. In an embodiment, the protein is present in an amount of about or equal to 175 mg/mL. In an embodiment, the protein is present in an amount of about or equal to 165 mg/mL. In an embodiment, the protein is present in an amount of about or equal to 162 mg/mL.

In yet another embodiment, a formulation of the invention comprises a concentrated protein in an amount greater than about or equal to 100 mg/mL and less than about or equal to 200 mg/mL, where the concentrated protein is an antibody; a salt in an amount of about 90 mM or about 95 mM, where the salt is sodium chloride; a buffer in an amount of about 20 mM, where the buffer is histidine and/or other forms of histidine; a surfactant in an amount of about 0.005% w/v, where the surfactant is a polysorbate; and, optionally, a sugar, a sugar alcohol, a mono- or disaccharide, or a combination thereof, in an amount of about 0.3% w/v to about 1.5% w/v. In an embodiment, the protein is present in an amount greater than about or equal to 100 mg/mL and less than about or equal to 180 mg/mL. In an embodiment, the protein is present in an amount of about or equal to 175 mg/mL. In an embodiment, the protein is present in an amount of about or equal to 165 mg/mL. In an embodiment, the protein is present in an amount of about or equal to 162 mg/mL.

In another embodiment, a formulation of the invention comprises a concentrated protein in an amount greater than about or equal to 100 mg/mL and less than about or equal to 200 mg/mL, where the concentrated protein is an antibody; a salt in an amount of about 90 mM or about 95 mM, where the salt is sodium chloride; a buffer in an amount of about 20 mM, where the buffer is a combination of glycine and histidine and/or other forms of glycine or histidine; a surfactant in an amount of about 0.005% w/v, where the surfactant is polysorbate; and, optionally, a sugar, a sugar alcohol, a mono- or disaccharide, or a combination thereof, in an amount of about 0.05% to about 1.8% w/v. In an embodiment, the protein is present in an amount greater than about or equal to 100 mg/mL and less than about or equal to 180 mg/mL. In an embodiment, the protein is present in an amount of about or equal to 175 mg/mL. In an embodiment, the protein is present in an amount of about or equal to 165 mg/mL. In an embodiment, the protein is present in an amount of about or equal to 162 mg/mL.

In another embodiment, a formulation of the invention comprises a concentrated protein in an amount greater than about or equal to 100 mg/mL and less than about or equal to 200 mg/mL, where the concentrated protein is any desired protein, such as, but not limited to, an antibody or a fragment thereof, a blood clotting factor, an enzyme, a peptide, a polypeptide, or combinations thereof; a salt and a buffer in a combined amount of from about or equal to 100 mM to about or equal to 120 mM, or from about or equal to 100 mM to about or equal to 110 mM, or from about or equal to 100 mM to about or equal to 115 mM, wherein the salt is, for example, sodium chloride, sodium gluconate, sodium lactate, or combinations thereof and the buffer is, for example, an amino acid such as glycine, histidine, or a combination thereof, or an organic acid such as succinic acid, maleic acid, tartaric acid, citric acid, acetic acid, or a combination thereof; and a surfactant in an amount of about 0.001% to about 0.2%, for example, a nonionic detergent, polysorbate, Pluronic, and the like, or a combination thereof.

The formulation may further comprise a sugar, a sugar alcohol, a monosaccharide, a disaccharide, or a combination thereof, which acts as tonicifier, in an amount of greater than about or equal to 0.05% w/v and less than about or equal to 1.8% w/v, or in an amount of greater than about or equal to 0.2% w/v and less than about or equal to 1.8% w/v, wherein nonlimiting examples include sorbitol, mannitol, sucrose, trehalose, or a combination thereof. In an embodiment, the tonicifier is present in an amount sufficient to provide an osmolality of the formulation of about 260 mOs/kg to about 280 mOs/kg. In an embodiment, the protein is present in an amount greater than or equal to 100 mg/mL and less than or equal to 200 mg/m L. In an embodiment, the protein is present in an amount of about or equal to 180 mg/mL. In an embodiment, the protein is present in an amount of about or equal to 175 mg/mL.

In accordance with the invention, and without wishing to be bound by theory, the salt and the sugar, sugar alcohol, mono- and/or di-saccharide, or combinations thereof, can function as tonicifiers in the described formulations. In some embodiments, the buffers, particularly the amino acid buffers, can also function as tonicifiers in the formulations. Such tonicifiers serve to achieve a suitable osmolality of the formulations.

The liquid formulations of the invention are of low viscosity. In general, the low viscosity formulations are manipulable through a 25 g to 27 g syringe needle, preferably a thin walled syringe, and are typically about 50 cps to about 60 cps. In an embodiment, the viscosity of the formulations is less than about or equal to 40 cps.

In an embodiment, the viscosity of the formulations is less than about or equal to 50 cps.

The liquid formulations of the invention are hypotonic and have an osmolality of less than 290 milliOsmoles (mOsm). In general, isotonicity is equivalent to a value of approximately 290 mOsm. In an embodiment, the osmolality of the formulations of the invention is about 240 mOsm to about 270 mOsm. In an embodiment, the osmolality of the formulations of the invention is about 250 mOsm to about 260 mOsm.

The pH of the formulations of the invention ranges from about or equal to pH 5.4 to about or equal to pH 6.4, or from about or equal to pH 5.4 to about or equal to pH 6.0, or from about or equal to pH 5.4 to about or equal to pH 5.6, or from about or equal to pH 5.4 to about or equal to pH 5.5.

In accordance with the invention, the described formulations are stable at a temperature of about 2° C. to about 8° C. for at least two months or longer, i.e., for over six months, for about one year, for over one year, for over eighteen months, or for over two years. As used herein, a stable formulation is one in which the structural integrity of the protein remains at least about 90% intact, substantially free of aggregates and/or degradation products, and optimally in which at least about 90% of the protein activity is maintained. The structural integrity of the protein may be evaluated by various biophysical methods, including, but not limited to, IEF gel, capillary IEF, ion exchange, HPLC, TSK gel filtration chromatography (TosoHaas, Montgomeryville, Pa.), sodium dodecyl sulfate-polyacrylamide gel electrophoresis (SDS-PAGE), by measuring the protein concentration as the net UV absorbance at a wavelength of 280 nm, and by visible inspection of liquid formulations for the presence of particulates against light and dark backgrounds. Methods for determining protein activity may be accomplished by, for example, initial rate experiments, progress curve experiments, transient kinetics experiments, and relaxation experiments.

In another embodiment of the invention, the formulation is substantially free of aggregates and/or degradation products. Substantially free refers to about 10% or less of aggregates and/or degradation products, or about 4% or less of aggregates and/or degradation products, or about 3% or less of aggregates and/or degradation products. In another embodiment, the formulation contains about 2% or less of aggregates and/or degradation products. In the formulations of the invention the concentrated protein is in its intended structural formation or a conformation that is functional and/or beneficial for treating a subject in need thereof. In the formulations of the invention, the concentrated protein is in a conformation that allows for its activity as an active ingredient in the formulation and its function following delivery or administration to a subject or individual in need thereof.

In an embodiment of invention, the formulation is substantially free of deamidation and/or degradation products. Substantially free refers to about 20% or less deamidation and/or degradation products, and/or changes in isoform distribution, or about 10% or less deamidation and/or degradation products, and/or changes in isoform distribution. In another embodiment, the formulation contains about 5% or less deamidation and/or degradation products, and/or changes in isoform distribution.

In all of the above embodiments, additional components may optionally be added to the formulations of the invention. Examples of such components are those that are useful in modifying the viscoelastic properties, thereby allowing for superior manufacturability and delivery of the formulation and its components to a subject. The additional components optimally do not interfere with the function or activity of the active ingredient(s) and other ingredients in the formulations. Non-limiting examples of optional or additional components are provided hereinbelow.

Concentrated Protein

While the formulations of the invention may include any protein, peptide, polypeptide, or antibody useful in a therapeutic or pharmacologic formulation, the formulations are most useful for concentrated proteins, i.e., proteins that are present in the formulations at a high concentration. Desirably, the protein is essentially isolated or purified and substantially free from undesirable contaminants. The highly concentrated protein may have a concentration greater than about or equal to 100 mg/mL to about or equal to 200 mg/mL. The highly concentrated protein may have a concentration of about or equal to 185 mg/mL, about or equal to 180 mg/mL, about or equal to 175 mg/mL, about or equal to 170 mg/mL, or about or equal to 165 mg/mL. More specifically, the protein is present in the formulations in an amount of 150 mg/mL to 200 mg/mL, or in an amount of 1 mg/mL increments from 150 mg/mL up to 200 mg/mL, e.g., 151 mg/mL, 152 mg/mL, 152 mg/mL, 153 mg/mL, 154 mg/mL, 155 mg/mL, 156 mg/mL, 157 mg/mL, 158 mg/mL, 159 mg/mL, 160 mg/mL, 161 mg/mL, 162 mg/mL, 163 mg/mL, 164 mg/mL, 165 mg/mL, etc.

The use of large, complex protein molecules as therapeutic agents has been of increasing interest, particularly as therapeutics and medicaments. The length of protein sequences may be, for example, anywhere from 100 to 1,000 amino acids, where the amino acid sequence typically dictates a protein's structural conformation. Internal bonds such as sulfur and hydrogen bonds can provide the protein its ultimate shape and form. Complex proteins may be further processed by the addition of phosphate groups, known as phosphorylation, or carbohydrate molecules, known as glycosylation, which modify the function of proteins. These proteins may be critical in cell biology and thereby have potential therapeutic uses in preventing, treating, and possibly even curing diseases and disorders. These proteins may include, but are not limited to, enzymes or blood factors that affect heart attacks, strokes, cystic fibrosis, Gaucher's disease; erythropoietin for anemia; blood clotting factors for hemophilia; or, insulin for treating diabetes all of which may be useful in the inventive formulation.

The concentrated proteins that can be used in the formulations of the invention include antibodies. Antibodies useful in the inventive formulation include, but are not limited to, polyclonal, monoclonal, diabodies, nanobodies, monovalent, bispecific, heteroconjugate, multispecific, autoantibodies, human, humanized or chimeric antibodies, single chain antibodies, Fab fragments, F(ab)'2, fragments, fragments produced by a Fab expression library, anti-idiotypic (anti-Id) antibodies, epitope-binding fragments and CDR-containing fragments or portions of any of the above. In an embodiment, the antibody is a humanized monoclonal antibody as described in U.S. Pat. No. 7,122,185, issued Oct. 17, 2006, the contents of which are incorporated by reference herein. A formulation containing such antibody may be used in the treatment of HIV-infected individuals.

Antibodies refer to immunoglobulin molecules and portions of immunoglobulin molecules that are immunologically active, i.e., molecules that contain an antigen binding site that specifically binds an antigen or immunogen. The immunoglobulin molecules of the invention can be of any type or isotype (e.g., IgA, IgD, IgE, IgG, IgM, and IgY), class or subclass (e.g., IgG1, IgG2, IgG3, IgG4, IgA1 and IgA2) of immunoglobulin molecules. Moreover, in addition to antibodies, functional antibody fragments (such as, for example, Fab, Fab', F(ab')$_2$, or Fd fragments, single-chain Fvs (scFv), single-chain antibodies, disulfide-linked Fvs (sdFv) and fragments comprising either a VL or VH domain, antigen-binding antibody fragments, including single-chain antibodies, which may comprise the variable region(s) alone or in combination with the entirety or a portion of the following: hinge region, CH1, CH2, and CH3 domains are also contemplated in the formulations described herein. Products of an Fab or immunoglobulin expression library, as well as, chimeric, single chain, and humanized antibodies may be useful in the instant formulation.

The antibodies of the invention may be from any mammalian origin. Non-limiting antibodies include those that are human, canine, feline, murine (e.g., mouse and rat), monkey, donkey, rabbit, goat, guinea pig, bovine, swine, horse, chicken, or the like that would be useful. These antibodies may be isolated from, for example, human immunoglobulin libraries or from mammalians transgenic for one or more human immunoglobulin and that do not express endogenous immunoglobulins. The antibodies useful in the instant formulation may be monospecific, bispecific, trispecific or of greater multispecificity. Multispecific antibodies may be specific for different epitopes of a particular polypeptide or may be specific for both a specific polypeptide as well as for a heterologous epitope, such as a heterologous polypeptide or solid support material.

Antibodies, or functional fragments thereof, can be used and have been found effective in treating numerous diseases or conditions, such as for example, various oncology-related diseases, virology-related or infectious diseases, gastroenterology-related diseases or conditions, heart disease, inflammation, transplantation rejection, skin, blood, neurological, respiratory, allergic and autoimmune disorders, and more specifically, for example, breast cancer, non-Hodgkin's lymphoma, prostate cancer, rheumatoid arthritis, respiratory syncytial virus, flaviviruses, particular viruses such as all strains and genotypes of HIV, HCV, HBV, HAV, HEV, HPV, HSV, and the like. Antibodies that target cell surface receptors, e.g., growth factor receptors and receptors involved in cell-to-cell contact or cell stimulation/proliferation, or other cell-surface target molecules are particularly useful in treating a number of diseases, such as cancers, tumors, cell proliferative diseases and the like. Such antibodies are suitable for use in the formulations of the invention. Antibodies have also been produced against dental caries, cholera, E. coli diarrhea, malaria, Norwalk virus, rhinovirus, influenza, and are useful in the described formulation. Antibodies, or fragments thereof, directed against bacterial toxins, such as toxin(s) produced by bacteria, e.g., *Staphylococcus, Streptococcus, Campylobacter, Clostridium*, and the like may be used in the formulations of the invention to treat infection or disease caused by these microorganisms. In particular, the formulations and compositions described herein may comprise antibodies, including monoclonal antibodies, humanized antibodies, or fragments thereof, directed against toxin A or toxin B of *Clostridium difficile*, or domains thereof. Additionally, antibodies such as the anti-CCR5 humanized monoclonal antibody PRO 140, or antibodies directed against prostate specific membrane antigen (PSMA), may be useful in the protein formulations described herein. The antibodies may be linked, coupled, or conjugated to other molecules, such as a toxin, small molecule drug or drug-like molecule, to enhance their therapeutic potency, effectiveness and/or utility.

The protein, or concentrated amount of protein, used in the formulations of the invention may be produced by any of several known techniques. This can be accomplished for example, by transforming or transfecting suitable host cells with an expression or cloning vector containing a nucleic acid encoding the protein of interest and culturing in conventional media with or without modification as necessary to induce the promoters, isolating the protein from an endogenous source, or synthetically through recombinant techniques and peptide synthesis or a combination of these techniques. The culture conditions, such as the media, temperature, pH, agitation speeds, and the like, can be selected by the skilled artisan without undue experimentation. Generally, the principles, protocols and practical techniques for optimizing the productivity of cell cultures can be found in Mammalian Cell Biotechnology: A Practical Approach, M. Butler, Ed., New York: IRL Press, 1991) and Sambrook et al., Molecular Cloning: A Laboratory Manual, Cold Spring Harbor, N.Y.: Cold Spring Harbor Laboratory Press, 2000. Where the concentrated protein used in the instant formulation is an antibody, those of ordinary skill in the art are familiar with the techniques for the production of antibodies, such as but not limited to, including polyclonal, monoclonal, humanized, bispecific and heteroconjugate antibodies, and the like.

The structural stability of the concentrated protein against changes in certain variables, namely pH, temperature, ionic strength, shear stress and freeze/thaw cycling may be evaluated using art-recognized methods and procedures.

Buffers and Tonicifiers

Tonicifiers or tonicifying agents are used to adjust the tonicity of the formulation. For a hypotonic formulation, the tonicity of the formulation must be adjusted such that the tonicity is less than that of an isotonic formulation. Typically, the concentration of only solutes that cannot cross the membrane dictates the tonicity of the formulation. The formulations of the invention comprise components that function as tonicifiers to obtain formulations and compositions that have low viscosity and are stable and hypotonic. While buffers stabilize the formulations, it was found that the presence of a salt served to decrease the viscosity of the formulations. The salts and buffers in the formulations are physiologically and pharmaceutically acceptable, such as a variety of commonly known and used acids or base-forming metals, amines and amino acids.

Non-limiting examples of salts useful in the instant formulations include ammonium chloride, ammonium sulfate, ammonium thiocyanate, arginine hydrochloride, calcium, calcium chloride, magnesium chloride, sodium acetate, sodium chloride, sodium gluconate, sodium lactate, sodium thiocyanate, zinc chloride, combinations thereof, and the like.

Buffers that are useful in the formulations of the invention include acids, e.g., maleic acid, succinic acid, citric acid, tartaric acid, acetate acid; bases; and/or amino acids. Examples of amino acids (amino acid buffers) include glycine, histidine, histidine monohydrochloride, combinations thereof, and the like. Suitable amino acids further include forms such as L-amino acids, and may include mono hydrochlorides, dihydrochlorides, and the like. In various embodiments, the other forms of glycine or histidine include, but are not limited to, the L-forms of these amino acids, monohydrochloride forms of these amino acids, combinations thereof, and the like. For example, glycine includes glycine, glycine monohydrochloride and L-glycine monohydrochloride, and histidine includes histidine, histidine monohydrochloride and L-histidine monohydrochloride. In an embodiment, the salts and buffers of the formulations are monovalent. In various embodiments, the one or more amino acids may be present in the formulations in an amount of from about 5 mM to about 20 mM, from about 5 mM to about 25 mM, from 5 mM to 20 mM, or from 5 mM to 25 mM.

In an embodiment, one or more amino acids are present in the formulation at a concentration of about or equal to 20 mM or 25 mM. Without wishing to be bound by theory, the amino acids provide buffering and/or stabilizing properties in the formulations of the invention. In an embodiment, the amino acid stabilizing or buffering agent is glycine or histidine, a combination of glycine and histidine, and/or other forms of glycine or histidine, e.g., L-glycine monohydrochloride, L-histidine monohydrochloride. In other embodiments, other amino acids may be used in combination in the formulations. In an embodiment, the formulation contains histidine and/or its other forms in combination with glycine and/or its other forms such that the total amount of these amino acids in combination is about or equal to 20 mM, or about or equal to 25 mM. Illustratively and without limitation, one of the amino acids may be present in an amount of about or equal to 5 mM and the other amino acid may be present in an amount of about or equal to 15 mM; similarly, one of the amino acids may be present in an amount of about or equal to 10 mM and the other amino acid may be present in an amount of about or equal to 15 Mm.

Non-limiting examples other agents that may be included in the formulations of the invention and/or utilized as buffers include inorganic and organic acids, inorganic and organic bases, carbonic, hydrobromic, hydrochloric, hydroiodic, nitric, perchloric, phosphoric, sulfanilic, sulfinic, sulfonic, sulfuric, straight and branched-chain alkyl, aromatic, arylaliphatic, saturated, unsaturated, mono, di- and tri-carboxylic, 1,2-ethanedisulfonic, 2-acetoxy-benzoic, 2-hydroxyacetic, 2-hydroxyethanesulfonic, 2-hydroxypropanoic, 2-oxopropanoic, 3-(4-hydroxybenzoyl)benzoic, 3-phenylpropionic, 4,4'-methylenebis-3-(hydroxy-2-ene-1-carboxylic acid), 4-chorobenzenesulfonic, 4-methylbicyclo[2.2.2]-oct-2-ene-1-carboxylic, acetate, acetic, anthranilic, ascorbic, benzenesulphonic, benzoic, butandioic, butanoic, camphorsulphonic, cinnamic, citric, cyclic, cycloaliphatic, cyclopentanepropionic, embonic, ethanesulphonic, formic, fumaric, glucoheptonic, gluconic, glycine, glycolic, glyconic, glyoxalic, HEPES, heterocyclic, histidine, hydroxymaleic, hydroxynapthoic, lactic, lauryl sulfuric, maleic, malic, malonic, mandelic, mesylic, methanesulphonic, muconic, napthalene-2-sulphonic, oxalic, palmeic, palmoic, phenylacetic, phthalic, propandioic, propanoic, p-toluenesulphonic, pyruvic, salicylic, stearic, succinate, succinic, succinic, tartaric, t-butyl acetic, thiocyanic, trifluoroacetic, trimethylacetic, or combinations thereof. Additional examples that are useful in the formulation include, but are not limited to, 2-diethylaminoethanol, alanine, aluminum, ammonium, arginine, asparagine, betaine, caffeine, caffeine, calcium, choline, copper, dicyclohexylamine, dicyclohexylamine, diethylamine, diethylamine, ethanolamine, ethanolamine, ethylenediamine, glucosamine, glutamine, glutamic acid, glycine, histidine, hydrabamine, iron, isopropylamine, isopropylamine, leucine, lithium, lysine, magnesium, manganese, methylglucamine, morpholine, N-ethylpiperidine, N-methylglucamine, phenylalanine, piperazine, piperidine, piperidine and organic nontoxic bases including, polyamine resins, potassium, primary, procaine, purines, secondary and tertiary amine, serine, sodium, substituted amines, theobromine, threonine, triethylamine, trimethylamine, tripropylamine, zinc, cyclic amines and basic ion exchange resins, for example, N(R')4+ (where R' is independently H or $C_{1-4}$ alkyl, e.g., Tris and ammonium), L-forms of amino acids, monohydrochlorides or dihydrochlorides of amino acids, combinations thereof, and the like.

In an embodiment, the formulations of the invention include one or more non-salt compounds or agents as tonicifying agents. Nonlimiting examples of suitable tonicifying agents also include compounds that may be known and used in the art as lyoprotectants. More specifically, suitable non-salt tonicifying agents include one or more monosaccharides and/or disaccharides. Formulations of the invention may contain one or more stabilizing, tonicifying agents, in a weight/volume (w/v) amount of about 0.05% to about 2%, in an amount of about 0.1% to about 1.8% w/v, in an amount of about 0.1% to about 1.5% w/v, in an amount of about 0.2% to about 2% w/v, in an amount of about 0.3% to about 2% w/v, or in an amount of about 0.5% to about 2%. More specifically, monosaccharides may be present in the formulations of the invention in an amount of about 0.2% w/v to about 1.5% w/v, in an amount of 0.15% to 1% w/v, or in an amount of 0.1% to 0.9% w/v. Disaccharides may be present in the formulation of the invention in the amount of about 0.4% to about 3% w/v, in an amount of 0.3% to 2% w/v, or in an amount of 0.2% w/v to 1.8% w/v. The amount of stabilizing agent may be determined to provide stability, while not decreasing intermolecular interactions.

Examples of useful tonicifying agents include, but are not limited to, monosaccharides, disaccharides, sugar, sugar alcohol, arabitol, betaine, cellobiose, dextran, di-fructose, di-glucose, erythritol, fructose, gelatin, glucitol, glucose, glycerin, glycerol, maltose, maltulose, iso-maltulose, lactitol, lactose, lactulose, lyotropic salt, magnesium sulfate, maltitol, mannitol, mannotriose, stachyose, melezitose, melibiose, methylamine, monoglycosides, monosodium glutamate or histidine, PLURONICS®, POLOXAMER 188 (Pluronics®188), polyethylene glycol, polyol, propylene glycol, raffinose, sorbitol, sucrose, trehalose, trihydric, turanose, xylitol, or combinations thereof.

One embodiment relates to formulations comprising buffers selected from any of the amino acids or a combination of amino acids in which the amino acids are characterized, for example, by charge, such as nonpolar/neutral; polar/positive; polar/neutral; and polar/negative. In a particular embodiment, the buffer is a single amino acid or an amino acid combination that is nonpolar/neutral or polar/positive.

In some embodiments, the salt and buffer(s), which comprise a salt/buffer tonicifier in the formulations of the invention, are present in amounts that in combination do not exceed 115 mM or 120 mM. The viscosities of formulations of the invention were measured at various salt concentrations, as described in Example 2 herein. The viscosity of a formulation of the invention, in some embodiments, is measured by the method described in Example 2 herein.

A further embodiment relates to formulations containing one or more buffers, such as one or more amino acids, at a concentration of 20 mM. Such formulations were surprisingly found to have a significant effect on the viscoelastic properties of the concentrated protein, e.g., an antibody. In an embodiment, the formulation comprising a concentrated protein, e.g., an antibody, is subjected to ultrafiltration and diafiltration processes used to remove small impurities from biological products. In the concentrated protein formulations, the presence of one or more nonpolar/neutral amino acid buffering agents at a total concentration of 20 mM reduced the processing time of ultrafiltration and diafiltration from about 3.5 hours to about 2.5 hours for 100 g of protein. The maximal protein concentration during ultrafiltration was found to be lower in those formulations containing one or more nonpolar/neutral amino acid buffers compared with formulations without such buffers, which suffered from high viscosity. The stable, low viscosity formulations useful for highly concentrated proteins as described herein provided advantages in the form of improved manufacturability and the ability to use the high concentration protein formulations in devices for manufacture and/or administration. Example 3 herein demonstrates the effects of buffers and buffer concentration on the overall viscosity of the formulations.

Surfactants

Surfactants are generally used in the formulations of the invention to avoid aggregation and particulate formation during processing or storage. Non-limiting examples of suitable surfactants include nonionic surfactants such as detergents, cetyl-betaine, cocamidopropyl-betaine, copolymers of ethylene and propylene glycol, pluronics (e.g., Pluronics®, PF68, etc.), disodium methyl oleyl-taurate, isostearamidopropyl-betaine, isostearamidopropyl-dimethylamine, lauroamidopropyl-betaine, lauryl-sarcosine, lauryl-sulfobetaine, linoleamidopropyl-betaine, linoleylmyristyl-betaine, linoleyl-sarcosine, linoleyl-sulfobetaine, MONAQUA™ series (Mona Industries, Inc., Paterson, N.J.), myristamidopropyl-betaine, myristamidopropyl-dimethylamine, myristyl-sarcosine, myristyl-sulfobetaine, palmidopropyl-betaine, palmidopropyl-dimethylamine, polyethyl glycol, polyethylene glycol, polyoxamers (e.g. Poloxamer® 181 or 188), polypropyl glycol, polysorbates (e.g. polyoxyethylene sorbitan monolaurate or polysorbate-20 (Tween® 20), polyoxyethylene sorbitan monopalmitate or polysorbate-40 (Tween® 40), polyoxyethylene sorbitan monostearate or polysorbate-60, polyoxyethylenesorbitan monooleate or polysorbate-80 (Tween® 80), or combinations thereof), sodium methyl cocoyl-taurate, sodium octyl glycoside, stearyl-sarcosine, stearyl-sulfobetaine, Triton®.

The amount of surfactant added to the formulation will vary and can be calculated and/or adjusted in amount such that there is reduced particulate formation in the formulation. In the solution or liquid formulations of the invention, surfactant may be present in an amount of about or equal to 0.001% to about or equal to 0.2% w/v, or in an amount of about or equal to 0.005% to about or equal to 0.2% w/v, or in an amount of about or equal to 0.05% to about or equal to 0.2% w/v. Illustratively, the surfactant is sucrose, sorbitol, mannitol, trehalose, glycerol, maltose, lactose, or a combination thereof. Disaccharides, such as maltose and lactose, contain a reducing sugar, which may not be as desirable as other suitable surfactants.

Other pharmaceutically and physiologically acceptable additives, carriers, excipients, or stabilizers may be included in the described formulations. These may be selected from those known in the art or as described in Remington: The Science and Practice of Pharmacy 21st ed., Philadelphia, Pa., David B. Troy Ed., Lippincott Williams & Wilkins (2005).

Formulation Characteristics

Osmolality/Tonicity

The formulations of the invention are hypotonic, where the osmolality of the formulations is less than the osmolality of a formulation that is isotonic or hypertonic, wherein an isotonic osmolality is about 290 mOsm/kg, for example, and a hypertonic osmolality is >290 mOsm/kg, for example. Because of their low viscosity, the formulations are provided for administering or delivering a high concentration of protein to a subject, particularly via subcutaneous administration. Additionally, because of their low viscosity, the formulations can be administered without causing undue pain or tissue irritation to the injected or inoculated subject. In one embodiment, a formulation of the invention has an osmolality of less than about 290 mOs/kg. In an embodiment, a formulation of the invention has an osmolality of less than about 280 mOs/kg. In another embodiment, a formulation of the invention has an osmolality of from about 225 mOs/kg to about 280 mOs/kg, from about 235 mOs/kg to about 265 mOs/kg, or of from about 240 mOs/kg to about 260 mOs/kg. In other embodiments, the formulations of the invention have an osmolality of 230 mOs/kg, 240 mOs/kg, 250 mOs/kg, or 260 mOs/kg. Osmolality may be measured by freezing point depression (Advanced® Model 3320 Micro Osmometer; Advanced Instruments Inc.; Norwood, Mass.). In some embodiments, the osmolality of a formulation of the invention is measured by freezing point depression. The reagents of the formulations, e.g., tonicifiers, salts, buffers, stabilizing agents, may all be useful for modifying and adjusting osmolality of the formulations in order to result in the desired hypotonicity.

Viscosity

The formulations of the invention, which contain a high concentration of protein, are of low viscosity. In this aspect, the formulations described herein are especially advantageous over other types of formulations for subcutaneous administration. In an embodiment, the low viscosity formulations are manipulable through a 25 g to 27 g syringe needle, preferably a thin walled syringe/needle. In an embodiment, the formulations have a viscosity of about 30 cps to about 60 cps. In an embodiment, the formulations have a viscosity between about 40 cps to about 50 cps. In various embodiments, the viscosity of a formulation of the invention is less than or equal to 55 cps, less than or equal to 50 cps, less than or equal to 40 cps, or less than or equal to 30 cps. Illustratively, a formulation of the invention comprising a protein in a concentration of 200 mg/mL has a viscosity of about 40 cps; a formulation of the invention comprising a protein in a concentration of 175 mg/mL has a viscosity of about 20 cps.

In all embodiments, the viscosity of a formulation of the invention will be sufficiently low to enable proper and safe administration to a subject in need thereof. For example, the viscosity of a formulation containing a concentrated amount of protein does not interfere with subcutaneous administration to a subject. The viscosity of a formulation of the invention is selected such that the formulation may be used and stored under the desired conditions. Methods of measuring viscosity are well known in the art, and may utilize, for example, a falling ball viscometer (Gilmont® GV-2200; Thermo Fisher Scientific; Waltham, Mass.) a capillary viscometer or a rheometer. Specifically, a glass capillary viscometer, a Zahn cup, a Ford viscosity cup, a Stormer viscometer, vibrating viscometers, such as the Dynatrol, acoustic rheometer, or the like may be used for the measurement of viscosity. The viscosity of a formulation of the invention, in some embodiments, is measured by any of the above techniques.

pH

Formulations for highly concentrated proteins as described herein have a pH in a range greater than about or equal to pH 5.4 and less than about or equal to pH 6.4. In one embodiment, the pH of the formulation is about 5.4 to about 6.0. In one embodiment, the pH of the formulation is about or equal to pH 5.4 or about or equal to pH 5.5. The pH will be in a range that results in a formulation that is physiologically acceptable and suitable with respect to the requirements of the formulation. The various salts, buffers, surfactants and stabilizing agents may be used in the appropriate amounts so as to adjust the pH to the desired pH. For example, the ratio between the amino acid and its hydrochloride may be used to modify the solution to a pH of about 5.4 or about 5.5. A low pH, e.g., pH 5.4, can compensate for a low buffering capacity at a low buffer concentration and a high protein concentration, such as, for example, about 20 mM for buffer and 175 mg/mL for protein, during processing and storage. Example 2 hereinbelow exemplifies the viscosity of a formulation over a pH range. In accordance with the invention, the presence of a salt, e.g., NaCl, in the formulations as described herein alleviates a pH effect.

Method of Making the Formulations

The formulations of the invention may be prepared by methods commonly used and known in the art and should not be limited by the state of matter of the formulation. In fact, the concentrated protein formulation takes into consideration the desired volume and mode of administration in the preparation of such a formulation. Since the formulation will be administered to subjects, including humans, sterile technique is essential. Accordingly, an embodiment of the invention is directed to a sterile formulation used for in vivo administration. The formulation is prepared using sterile techniques known and commonly used in the art, for example, sterile filtration, autoclaving all non-protein components, and the like.

The concentrated protein for use in the formulation may be present in solution, for example, in a pH-buffered solution, such that the final hypotonic formulation has a pH ranging from about 5.4 to about 6.4. Exemplary buffers and/or salts are those that are pharmaceutically and physiologically acceptable and may be prepared from appropriate acids, bases and salts thereof, as mentioned hereinabove.

In other embodiments, the formulations of the invention may contain one or more proteins, if more than one protein is beneficial for a particular indication being treated, and in cases in which the presence of one protein does not adversely affect the other(s). Illustratively, two or more proteins may have complementary, additive, or synergistic activities. When these proteins are present in combination, they are in amounts that are effective for the intended purpose and that are in accordance with the formulations of the invention.

In an embodiment, the formulations described herein are in liquid form and are stored in solution. The formulations may include an excipient that is useful for stabilizing the stored formulation. Non-limiting examples of excipients include e.g., sugars, polymers, surfactants and amino acids. Some excipients are referred to and/or utilized in formulations as lyoprotectants and cryoprotectants. Formulations as solutions may also be frozen and stored. According to the invention, solution formulations may be optimally stored for at least 12 months, at least 18 months or longer, at a temperature ranging from about 2° C. to 8° C.

The protein-containing formulations of the invention have particular properties as characterized by their osmolality, viscosity and density. These properties may be measured by any known means. For example, osmolality may be measured by freezing point depression (Advanced® Model 3320 Micro Osmometer; Advanced Instruments Inc.; Norwood, Mass.); viscosity by a falling ball viscometer (Gilmont® GV-2200; Thermo Fisher Scientific; Waltham, Mass.) or a cone and plate viscometer (Brookfield), (Brookfield Engineering Laboratories, Inc., Middleboro, Mass.); and density by an oscillating densitometer (Densito 30PX; Mettler-Toledo Inc.; Columbus, Ohio). The viscosity and/or osmolality of a formulation of the invention, in some embodiments, is measured by any of these above techniques, respectively. Example 4 provides the results of these properties in relation to various protein concentrations in a formulation of the invention.

Uses of the Formulations of the Invention

The formulations of the invention contain one or more active ingredients, such as proteins, e.g., antibodies, that are useful in the treatment of a variety of diseases, conditions or disorders by administration to subjects in need thereof. The subjects may be, but are not limited to, mammals, non-human primates, human beings (called individuals, subjects, or patients herein), dogs, cats, horses, monkeys/chimpanzees, mice, rats, rabbits, chickens, donkeys, goats, guinea pigs, pigs, cows, sheep, and the like suffering from a disease, condition or disorder and in need of treatment. In fact, any active ingredient, such as a protein in a high concentration, is contemplated for use in the formulations of the invention, depending upon the disease, condition or disorder to be treated, alleviated, or cured.

Other embodiments include a concentrated protein which is also beneficial in formulations used in prophylactic treatment for a subject who is anticipated to be in need thereof, for example, a susceptible subject who is at risk of contracting a disease, condition or disorder. The formulations of the invention, which comprise various types of concentrated proteins, serve to deliver or administer the concentrated protein and are not meant to be limited to any particular application or disease. Concentrated proteins, such as antibodies, are particularly useful; thus, a formulation of the invention containing one or more antibodies, e.g., monoclonal antibodies, human antibodies, humanized antibodies, chimeric antibodies, and the like, in high concentration, for the treatment of a particular disease, condition or disorder is useful in the treatment of the particular disease, condition or disorder that is targeted by the antibody(ies). Any of the antibodies described herein or known in the art may be used in the formulations of the invention.

The formulations may be administered to a subject in need thereof by different means and in accordance with an optimal delivery method for a particular treatment. For example, administration may be by injection, bolus injection, or continuous infusion. The formulations or compositions may be administered by a number of routes of administration, such as, for example, intradermal, intramuscular, intraosseous, intravenous, intraperitoneal, parenteral, nasal, intraocular, subcutaneous, and the like. Other forms for administration include, without limitation, liquid, semi-solid, and solid dosage forms, such as liquid solutions (for example, injectable and infusible solutions), dispersions or suspensions, tablets, pills, powders, liposomes, and the like. The need for small volumes of highly concentrated proteins in a formulation, especially for subcutaneous injection, is met by the formulations described herein. For an injected formulation, injection/administration may be performed using, for example and without limitation, an infusor, infusion device, autoinjector, a jet injector, a syrette, syringe, a multishot or multidose needle syringe, a pre-filled syringe, a pre-filled multishot or multidose needle syringe or pen device, a pen, a pump, and the like. For simplicity or ease of use, it is useful to have a device containing a pre-filled, pre-determined amount of the inventive formulation containing the concentrated therapeutic. The device for administration may provide the formulation in a unit dosage form, in multiple dosages, or in a predetermined amount.

The formulations may be in a number of forms, such as but not limited to, suspensions, solutions or emulsions in oily or aqueous vehicles, and may contain formulatory agents, such as suspending, stabilizing and/or dispersing agents. In an embodiment, the suspensions and solutions are aqueous. Additionally, the active ingredient may be in dried, freeze-dried, lyophilized, or powder form for reconstitution with a suitable vehicle, e.g., sterile pyrogen-free water, buffer, or the like before use.

In one embodiment, the protein, e.g., an antibody, is formulated in accordance with routine procedures as a pharmaceutical formulation adapted for subcutaneous administration to subjects in need, such as for example, humans suffering from a disease that can be treated with a particular antibody, which must be administered to a subject in concentrated amounts in a reasonable volume. In general, formulations for subcutaneous administration are sterile aqueous solutions. Exemplary formulations of the invention and therapeutic application of the formulations via subcutaneous administration are described in Examples 2 and 6, respectively, herein.

Where necessary, a formulation or composition may also include a solubilizing agent, a preservative, and a local anesthetic such as lignocaine, lidocaine, or benzyl alcohol to ease potential pain at the site of the injection. Generally, formulation ingredients are supplied either separately or mixed together in unit dosage form, for example, as a dry lyophilized powder or water-free concentrate in a hermetically sealed container such as a vial or a two-chambered cartridge indicating the quantity of active agent. Alternatively, the formulation is in solution form in a suitable container or delivery device having a predetermined dosage. Where the formulation is to be administered by infusion, it can be dispensed with an infusion bottle containing sterile pharmaceutical grade water or saline. Where the formulation is administered by injection, a suitable delivery device, e.g., syringe or pre-filled syringe containing sterile water, saline, or buffer for injection, is provided so that the formulation may be mixed or reconstituted prior to administration. In other instances, the formulation containing a high concentration of protein is administered from a suitable delivery device without prior mixing or reconstitution. In an embodiment, the formulation is a solution containing a high concentration of protein and is delivered by a device without prior mixing or reconstitution.

The amount of the protein useful in a formulation of the invention is that which is effective in the therapy or treatment, reduction, abrogation, inhibition, amelioration, or elimination of a disease, disorder, or condition associated with, for example, aberrant or over-expression and/or activity of the target of the highly concentrated protein, generally as determined by standard clinical techniques. Similarly, the amount of protein useful in the formulation will be in an amount effective as a prophylactic agent. In vitro assays may optionally be employed to assist with the determination of the optimal dosage ranges. The precise dose to be employed in the formulation will also depend on the route of administration, and the criticality of the disease, disorder, or condition. The practitioner, utilizing his or her best judgment based on each subject's circumstances, can determine the best dosage and therapy for the subject in need. Effective doses may be extrapolated from dose-response curves derived from in vitro or animal (in vivo) model test systems.

For example, the dosage of a formulation containing antibodies administered to a subject is typically about 0.1 mg/kg to about 100 mg/kg of the patient's body weight, greater than about or equal to 0.1 mg/kg, or greater than about or equal to 1 mg/kg. In other embodiments, the dosage may be less than about or equal to 25 mg/kg of the patient's body weight, less than about or equal to 20 mg/kg of the patient's body weight, less than about or equal to 15 mg/kg of the patient's body weight, or less than about or equal to 10 mg/kg or 5 mg/kg or 2 mg/kg of the patient's body weight. Generally, human or humanized antibodies have a longer half-life within the human body than antibodies from other species due to the immune response to the latter foreign polypeptides. Thus, lower dosages of human or humanized antibodies and less frequent administration are often possible. Further, the dosage and frequency of administration of antibodies utilizing the formulations of the invention may be reduced by enhancing uptake and tissue penetration of the antibodies by modifications, for example, lipidation as a means to better target brain cells and tissues. However, the skilled practitioner, based on dose-response data and experience, has the knowledge and means for determining the best dosage protocol to treat the subject in need. Used as a prophylactic agent, the dosage amount and protocol can also be determined by the skilled practitioner.

The formulations of the invention may be used in combination with one or more additional or other therapeutics, therapeutic agents, medicaments, or drugs. For example, co-administration to a subject in need of a highly concentrated protein with an agent A and/or an agent B, for example, is embraced by the invention, in which the additional agent(s) is/are dissolved or intermixed in the same formulation of the invention. Alternatively, the protein-containing formulation of the invention is administered to a subject, followed by the administration of agent A, followed by the administration of agent B in separate formulations, or vice versa. The protein-containing formulations of the invention may be administered at the same time as, or at different times than, the one or more additional or other therapeutics that are co-administered. An embodiment of the invention includes methods of combination or concomitant therapeutic treatment and combination pharmaceutical formulations.

Article of Manufacture

Another embodiment of the invention relates to packaged pharmaceutical compositions which include a concentrated protein, such as, for example, a concentrated antibody, in the formulations described herein. Specifically, the packaged pharmaceutical composition, article of manufacture, or kit provides a formulation described herein and typically provides instructions for its use. The article of manufacture or kit comprises a container suitable to contain, and perhaps deliver or administer, the formulation. The package, article of manufacture or kit may comprise a single concentrated protein formulation, or one or more concentrated protein formulations, where the active agent or protein is presented either together in one formulation or separately in more than one formulation. Non-limiting examples of suitable containers include, bottles, vials, single or dual chamber vials, cartridges, syringes, single or dual chamber syringes, multishot or multidose needle syringes, jet injectors, pens, multidose pens, pumps, syrettes, autoinjectors, infusors, pre-filled syringes, test tubes, nebulizers, inhalers (e.g., metered dose inhalers or dry powder inhalers), depots, and the like. The container holding the formulation may be a device or syringe or pen having multiple doses, which allows for repeated administrations of a predetermined amount (e.g., from 2-10 doses) of the formulation.

In an embodiment, a sealable container may contain a formulation of the invention. In another embodiment, the formulation may be contained in a pre-filled syringe. In a further embodiment, the formulation may be contained in any of the above-described containers suitable for delivering the formulation to a subject. In a further embodiment, the formulation may be contained within an infusion bag or a sealable bottle. In another embodiment, the formulation is suitable for parenteral administration, which may be performed intravenously, subcutaneously, or intramuscularly.

The container may be formed from a diverse range of materials, such as, but not limited to glass, metal, plastic (e.g., polycarbonate, polystyrene, polypropylene), or any other material suitable for containing the formulation without any unfavorable reaction to the components or active ingredients therein. Either on or associated with the container, a label with directions for use, ingredients, and/or side effects is provided. The label may include formulation ingredients, indications, usage, dosage, administration, as well as warnings, precautions, side effects, adverse reactions, and drug interactions The article of manufacture may have additional containers. For example, a second container any contain a suitable carrier, diluent, excipient, vehicle, or buffer.

The containers packaged in the article of manufacture may be presented singly or in a pack or dispenser device, comprising metal or plastic foil, such as a blister pack. Moreover, the pack or dispenser device, containers, and formulations may be presented in a kit for commercial distribution with a label with instructions, ingredients, and/or warnings. The container may also contain one or more predetermined unit dosages of the formulation. The article of manufacture also contains a label or package insert on or associated with the container.

Another embodiment is directed to additional therapeutic agents, medicaments, drugs, or compounds, which may be included in the stable, low viscosity protein formulation of the invention. These additional components may be active agents or ingredients that do not adversely react with the other concentrated protein of the formulation. Rather, these active agents provide additional benefits to treat a subject afflicted with a given disease, disorder, or condition and in need of treatment. Since there may be numerous biological pathways that lead to the same disease, disorder or condition, the use of multiple agents may allow their biological effects to treat the subject by similar or unrelated mechanisms of action. Thus, multiple active agents that diminish or treat at least one symptom associated with the same targeted disease may be utilized in the same formulation, or in multiple, separate formulations that are administered in combination. The administration of multiple active agents may have additive or synergistic effects or benefits.

Another embodiment of the invention relates to the use of the low viscosity protein formulations of the invention in combination therapies with other active agents, drugs, chemotherapy and/or radiation therapy. The concentrated protein formulations may be provided with one or more other active agents and/or chemotherapy and/or radiation therapy in a prior, subsequent, or simultaneous administration.

Other Embodiments

In an aspect, the invention provides a low viscosity formulation, composition, or preparation comprising a concentrated protein, i.e., present in the formulation at a high concentration, wherein the protein is in an amount of about 100 mg/mL to about 200 mg/mL; a salt, which, without wishing to be bound by theory, functions as a tonificier herein, present in an amount of less than or equal to 100 mM, about or equal to 90 mM, or about or equal to 95 mM, a buffer present in an amount of from about or equal to 5 mM to about or equal to 20 mM; and a surfactant in an amount of about 0.001% to about 0.2%. In some embodiments, the formulation also comprises a non-salt tonicifying agent or tonicifier. In various embodiments, the non-salt tonicifier is, illustratively, a sugar, a sugar alcohol, a monosaccharide, a disaccharide, or a combination thereof, present in an amount sufficient to provide an osmolality of about 230 mOs/kg to about 280 mOs/kg. In an embodiment, the formulation, composition, or preparation is hypotonic. In an embodiment, the formulation, composition, or preparation is in liquid or solution form.

In another aspect, the invention provides a low viscosity, formulation, composition, or preparation comprising a concentrated protein, or a high concentration of protein, wherein the protein is in an amount of about 100 mg/mL to about 200 mg/mL; a salt and a buffer present in combination (salt/buffer), wherein the combination of salt and buffer is in an amount of about 100 mM to about 120 mM, in an amount of about 100 mM to about 115 mM, in an amount of about 100 mM to about 110 mM, in an amount of 100 mM to 120 mM, in an amount of 100 mM to 115 mM, or in an amount of 100 mM to 110 mM; and a surfactant in an amount of about 0.005% to about 0.2% w/v. In some embodiments, the formulation also comprises a non-salt tonicifier. In various embodiments, the non-salt tonicifier is, illustratively, a sugar, a sugar alcohol, a monosaccharide, a disaccharide, or a combination thereof, and is present in an amount of about 0.05% w/v to about 1.8% w/v of the total formulation, or in an amount sufficient to provide an osmolality of about 230 mOs/kg to about 280 mOs/kg. In an embodiment, the formulation, composition, or preparation is hypotonic. In an embodiment, the formulation, composition, or preparation is in liquid or solution form.

The invention further encompasses a formulation comprising a concentrated protein, a salt and a buffer, wherein the salt and the buffer in combination are present in an amount of from about 110 mM to about 120 mM, and a surfactant wherein the formulation is of low viscosity. In an embodiment, the concentrated protein is in an amount greater than about or equal to 100 mg/mL and less than about or equal to 200 mg/mL. In an embodiment, the concentrated protein is present in an amount of about or equal to 162 mg/mL to about or equal to 175 mg/mL. In an embodiment, the concentrated protein is a peptide, an enzyme, a polypeptide, an antibody or a fragment of an antibody. In an embodiment, the concentrated protein is a monoclonal antibody, a polyclonal antibody, a nanobody, a hybrid antibody, or a fragment of an antibody. In an embodiment, the concentrated protein is a monoclonal antibody that is humanized, or a fragment of the humanized antibody. In an embodiment, the antibody or fragment thereof is directed against HIV, HCV, HIV or HCV polypeptides, or a cancer-related target molecule. In an embodiment, the salt is present in an amount of less than 100 mM or in an amount that is about or equal to 95 mM. In an embodiment, the salt may be one or more of ammonium chloride, ammonium sulfate, ammonium thiocyanate, arginine hydrochloride, calcium chloride, magnesium chloride, sodium acetate, sodium chloride, sodium gluconate, sodium lactate, sodium thiocyanate, zinc chloride, or any combination thereof. In an embodiment, the salt is sodium chloride. In an embodiment, the buffer is present in an amount of about 5 mM to about 20 mM. In an embodiment, the buffer is present in an amount of about or equal to 20 mM. In an embodiment, the buffer is one or more amino acids, or a derivative or an L-molecular form thereof. In an embodiment, the one or more amino acids are histidine, glycine, or a combination of histidine and glycine, or an L-molecular form thereof. In an embodiment, the surfactant is present in an amount of about or equal to 0.001% w/v to about or equal to 0.2% w/v. In an embodiment, the surfactant is present in an amount of about or equal to 0.005% w/v. In an embodiment, the surfactant may be a detergent, pluronic, polysorbate, polysorbate-20 (e.g., Tween®20), polyethylene glycol, or a combination thereof. In an embodiment, the formulation also contains a non-salt tonicifying agent, which may be present in the formulation in an amount from about 0.05% w/v to about 1.8% w/v of the total formulation. In an embodiment, such a tonicifying agent is a sugar, a sugar alcohol, a monosaccharide, a disaccharide, or a combination thereof. In an embodiment, the formulation has a viscosity of about 25 cps to about 60 cps, or a viscosity of about 40 cps to about 50 cps. In an embodiment, the formulation has a pH of from about 5.4 to about 6.4, or a pH of from about 5.4 to about 6, or a pH of 5.4 to 5.6. In an embodiment, the formulation has an osmolality of less than about 290 mOs/kg, or an osmolality of about 230 mOs/kg to about 280 mOs/kg, or an osmolality of about 260 mOs/kg.

In an embodiment, the formulation also comprises a therapeutic protein for administration to a subject in need thereof. In an embodiment, the formulation is administered by injection, bolus injection, intradermal, intramuscular, intraosseous, intravenous, or subcutaneous injection. In an embodiment, the formulation is administered by the use of a syringe, a pen, a pump, a cartridge, a two-chambered cartridge, a multishot needle syringe, a multidose needle syringe, a multidose pen, a jet injector, a syrette, an auto-injector, or a pre-filled syringe delivers the formulation. In an embodiment, the formulation is a liquid or solution formulation.

The invention further encompasses a formulation that includes a concentrated protein in an amount greater than about or equal to 100 mg/mL and less than about or equal to 200 mg/mL; a salt in an amount greater than about or equal to 90 mM and less than about or equal to 100 mM, or greater than about or equal to 95 mM and less than about or equal to 100 mM; a buffer in an amount greater than about or equal to 5 mM and less than about or equal to 25 mM; a surfactant in an amount greater than about or equal to 0.001% w/v and less than about or equal to 0.2% w/v; and, optionally, a non-salt tonicifier in an amount of about 0.05% w/v to about 1.8% w/v; wherein the formulation has an osmolality of about 250 to about 280 mOsm/kg. In an embodiment, the concentrated protein is an antibody or a fragment thereof, a blood clotting factor, an enzyme, a peptide, or a combination thereof. In an embodiment, the protein is a monoclonal antibody, a human monoclonal antibody, or a humanized monoclonal antibody. In an embodiment, the salt is sodium chloride, sodium gluconate, sodium lactate, or a combination thereof. In an embodiment, the buffer is glycine, histidine, succinic acid, maleic acid, citric acid, tartaric acid, or a combination thereof. In an embodiment, the surfactant is polysorbate-20 (polyoxyethylene 20 sorbitan monolaurate; commercially known as Tween®20), polysorbate-40 (polyoxyethylene (40) sorbitan monopalmitate; commercially known as Tween®40), polysorbate-60 (polyoxyethylene (60) sorbitan monostearate; commercially known as Tween®60), polysorbate-80 (polyoxyethylene (80) sorbitan monooleate; commercially known as Tween®80), or a combination thereof. In an embodiment, the non-salt tonicifying agent is selected from one or more of sorbitol, mannitol, sucrose, trehalose, glycerol, or a combination thereof. In an embodiment the formulation has a viscosity of about 25 cP to about 60 cP. In an embodiment the formulation has a viscosity of 25 cP to 60 cP In an embodiment, the formulation has a pH of from 5.4-6.4. In an embodiment, the formulation has an osmolality of about 240 mOs/kg to about 280 mOs/kg. In an embodiment, the formulation is a liquid or solution formulation.

The invention further encompasses a low viscosity, hypotonic, liquid formulation, which includes a concentrated protein in an amount greater than about or equal to 100 mg/mL and less than about or equal to 200 mg/mL, wherein the concentrated protein is an antibody or a fragment thereof; a salt in an amount of about or equal to 90 mM or 95 mM; a buffer in an amount of about or equal to 20 mM; a surfactant in an amount of about 0.005% w/v; and optionally a non-salt tonicifying agent in an amount of about 0.05% w/v to about 1.8% w/v. In an embodiment, the antibody is a monoclonal antibody or a humanized monoclonal antibody; the salt is sodium chloride; the buffer is glycine, histidine, or a combination thereof; the surfactant is polysorbate or pluronic; and the non-salt tonicifying agent is sorbitol, mannitol, sucrose, or trehalose.

The invention further encompasses a low viscosity hypotonic liquid formulation, which includes a concentrated antibody or fragment thereof in an amount greater than about or equal to 100 mg/mL and less than about or equal to 200 mg/mL; a salt in an amount of about or equal to 90 mM or about or equal to 95 mM, wherein the salt is sodium chloride; a buffer in an amount of about 20 mM, wherein the buffer is histidine; a surfactant in an amount of about 0.005% w/v, wherein the surfactant is polysorbate; and a non-salt tonicifying agent in an amount of about 0.3% w/v, wherein the non-salt tonicifying agent is sorbitol or sucrose.

The invention further encompasses a low viscosity hypotonic liquid formulation, which includes a concentrated antibody or fragment thereof in an amount greater than about or equal to 100 mg/mL and less than about or equal to 200 mg/mL; a salt in an amount of about or equal to 90 mM or about or equal to 95 mM, wherein the salt is sodium chloride; a buffer in an amount of about or equal to 20 mM, wherein the buffer is a combination of glycine and histidine; and a surfactant in an amount of about or equal to 0.005% w/v, wherein the surfactant is a polysorbate. In an embodiment, the formulation also includes a non-salt tonicifying agent in an amount of about 1% to 1.5% w/v, wherein the tonicifying agent is sorbitol or sucrose.

In accordance with the various embodiments of the invention, the described formulations have an osmolality of less than about 290 mOs/kg.

The invention further embraces an article of manufacture, which includes a container and a formulation comprising a protein in a concentration of greater than 100 mg/mL and less than 200 mg/mL, a salt and a buffer present in a combined amount of from about 110 mM to about 120 mM, a surfactant and instructions for use. In an embodiment, the formulation in the article of manufacture further comprises a non-salt tonicifying agent. In an embodiment, the container is selected from a bottle, a vial, a syringe, a pen, a pump, a multidose needle syringe, a multidose pen, a jet injector, a syrette, an autoinjector, a pre-filled syringe, or a combination thereof. In an embodiment, the formulation is included in the container of the article of manufacture.

EXAMPLES

The following examples further describe and demonstrate embodiments within the scope of the present disclosure. The examples are given solely for the purpose of illustration and are not to be construed as limitations of the present disclosure, as many variations thereof are possible without departing from the spirit and scope of the disclosure.

In the Examples below, the density, osmolality, and viscosity were measured using an oscillating densitometer (Densito 30PX; Mettler-Toledo Inc.; Columbus, Ohio); freezing point depression (Advanced® Model 3320 Micro Osmometer; Advanced Instruments Inc.; Norwood, Mass.), core and plate viscometer (Brookfield), (Brookfield Engineering Laboratories, Inc., Middleboro, Mass.), and falling ball viscometer (Gilmont® GV-2200; Thermo Fisher Scientific; Waltham, Mass.). Because there are various means for measuring these properties, the specified procedures and devices are not intended to be limiting. The density, osmolality and/or viscosity of a formulation of the invention, in some embodiments, is measured by any of these techniques, respectively.

Example 1

Low Viscosity Protein Formulations Containing a Highly Concentrated Protein

To prepare low viscosity formulations that contain a high concentration of protein and are hypotonic, the osmolality of the formulations was designed to be less than that of an isotonic formulation. In certain formulations, the osmolality was less than about 290 mOs/kg, less than about or equal to 260 mOs/kg, less than about or equal to 250 mOs/kg, or less than about or equal to 210 mOs/kg, compared with an isotonic formulation having an osmolality of about 290 mOs/kg.

Hypotonic liquid formulations comprising a concentrated antibody were formulated using 100-200 mg/ml of antibody. More specifically, the formulations contained an antibody in a concentration of 0 mg/ml, 75.3 mg/ml, 92.8 mg/ml, 126.3 mg/ml, 148.6 mg/ml, 175 mg/ml, 203.3 mg/ml, 216.9 mg/ml, and 225.8 mg/ml. Useful formulations comprising the concentrated protein had a viscosity of less than 75 cps, less than 50 cps, less than 25 cps, and less 15 cps. The formulations contained between 50 mM and 95 mM salt selected from sodium chloride, sodium lactate, sodium gluconate, or combinations thereof, and also included 5 mM to 20 mM of buffer, such as glycine, histidine, or combinations thereof. The concentration of the salt and buffer combination, i.e., salt/buffer tonicifier, was 65 mM to 115 mM. Certain preparations had a surfactant in an amount ranging from 0.001% to 0.2% w/v, while other preparations contained a surfactant in an amount of 0.005% w/v. The surfactants included polysorbate, i.e., polysorbate-20 (Tween20®). In some of the prepared formulations monosaccharides, disaccharides, sugar alcohols, or combinations thereof, were included as stabilizing and tonicifying agents in an amount ranging from 0.1% w/v to 5% w/v, more specifically, from 0.1% w/v to 1.8% w/v. Examples of stabilizing agents included sugars, such as sucrose and sorbitol, or synthetic compounds similar to natural sugars or sugar alcohols. The pH of the particular formulations ranged from pH 5.4 to pH 6.4. The formulations were prepared such that they were stable with a shelf life of at least 18 months at a temperature ranging from about 2° C. to about 8° C.

Exemplary formulations of the invention are those that are comprised of any combination of the following categories of ingredients: (A) Buffer (20 mM), e.g., glycine, histidine, glycine/histidine in any combination, tartaric acid, maleic acid, succinic acid, citric acid, acetate acid; (B) Salt (90 mM or 95 mM), e.g., NaCl, Na gluconate, Na lactate; (C) Tonicifier (up to ~260 mOs/kg), e.g., sugar alcohols, disaccharides, sorbitol, mannitol, sucrose, trehalose, glycerol, maltose, lactose; (D) Surfactant (0.001%-0.2% w/v), e.g., polysorbate 20 (Tween® 20), polysorbate 80 (Tween® 80), POLOXAMER 188 (Pluronics 188). Disaccharides such as maltose and lactose may be used, but may be less desirable as they contain reducing sugar.

Various solution or liquid formulations according to the invention were prepared in which the resulting formulation was hypotonic (less than about 290 mOs/kg) and of low viscosity. One hypotonic, low viscosity formulation was prepared to contain the anti-CCR5, humanized, monoclonal antibody PRO 140 at a concentration of 162 mg/ml; sodium chloride at a concentration of 95 mM; histidine at a concentration of 20 mM; Tween20® surfactant at a concentration of 0.005%; and sucrose at a concentration of 1.5%, pH 5.5. A second hypotonic, low viscosity formulation was prepared to contain the anti-CCR5, humanized, monoclonal antibody PRO 140 at a concentration of 162 mg/ml; sodium chloride at a concentration of 95 mM; glycine at a concentration of 20 mM; Tween20® surfactant at a concentration of 0.005%; and sucrose at a concentration of 1.5%, pH 5.5. A third hypotonic, low viscosity formulation was prepared to contain the anti-CCR5, humanized, monoclonal antibody PRO 140 at a concentration of 175 mg/ml; sodium chloride at a concentration of 95 mM; histidine at a concentration of 5 mM; glycine at a concentration of 15 mM; Tween20® surfactant at a concentration of 0.005%; and sorbitol at a concentration of 0.3%, pH 5.5. A fourth hypotonic, low viscosity formulation comprised the anti-CCR5, humanized, monoclonal antibody PRO 140 at a concentration of 175 mg/ml; sodium chloride at a concentration of 95 mM; succinic acid at a concentration of 20 mM; Tween20®surfactant at a concentration of 0.005%; and sucrose at a concentration of 1.5%, pH 5.5. A fourth hypotonic, low viscosity formulation comprised the anti-CCR5, humanized, monoclonal antibody PRO 140 at a concentration of 175 mg/ml; sodium chloride at a concentration of 95 mM; maleic acid at a concentration of 20 mM; Tween20® surfactant at a concentration of 0.005%; and sucrose at a concentration of 1.5%, pH 5.5.

Example 2

Formulation Viscosities at Various pH Ranges and Salt Concentrations

To study the roles of pH, buffer and tonicifier with respect to viscosity, four formulations were prepared. Antibody formulations containing a concentrated antibody of 154 mg/mL were observed over a pH range from pH 4 to pH 7.4. When comparing the characteristics of four different formulations containing the following buffers or salt/buffers: 20 mM histidine, histidine/glycine, NaCl/histidine and sucrose/histidine, the results demonstrated that the viscosity ranged from 10 cP to 30 cP. The isoelectric point of the antibody was pI 7.5, but when the antibody was in its charged, acidic form, the formulations containing histidine/glycine, sucrose/histidine and histidine only were found to have lower viscosities at a pH of less than 6. The concentration of the histidine buffer in these formulations was 20 mM. It was observed that there was no pH effect when a salt, i.e., an ionic tonicifier, was included in the formulation. Without wishing to be bound by theory, it was found that the presence of a salt decreased the inter-molecular interactions of the antibody and consequently, decreased the viscosity of the formulation.

Formulations containing proteins in two different concentrations greater than 100 mM and salt concentrations ranging from 0 mM to about 600 mM were found to have viscosities ranging from about 13 cP to 20 cP. When the formulations were compared and analyzed, it was found that the viscosities of the formulations were optimally decreased at a salt concentration of about 100 mM or less.

Example 3

Effects of Buffers on Viscosity at High and Low Shear Rates

Various formulations were tested for shear rates using a rheometer that could analyze a wide range of shear rates, e.g., 1×10-3 sec-1 to 1×104 sec-1. The sample formulations varied with respect to the types of buffers and combination of buffers, yet all of the formulations had the same total buffer concentration of 20 mM. At a high shear rate (1 to 100 sec-1), the formulations had viscosities ranging from 15 mPa·s to 17 mPa·s. For example, a polar/positive amino acid buffer formulation had the lowest viscosity, while a nonpolar/neutral buffer formulation had the highest viscosity. At a low shear rate (1×10-4 to 1 sec-1), the formulations had the opposite results, i.e., the polar/positive amino acid buffer formulation had the highest viscosity in the low shear rate experiment. At a low shear rate, the formulations had viscosities ranging from 1150 mPa·s to 4745 mPa·s. This difference in viscosities at low shear rates is an important factor in the manufacturing process of drug substances, drug products, and devices. Selecting the appropriate buffer affects manufacturing time and the final concentration of protein. An undesirable buffer can increase the manufacturing time and decrease the protein concentration. Specifically, a formulation containing a polar/positive amino acid buffer had a longer manufacture processing time and lower protein concentration, although still concentrated and greater than 100 mg/mL, compared to the formulation containing a nonpolar/neutral amino acid buffer. Such viscoelastic properties should be considered in connection with filtration, filling processes, and the delivery of a concentrated protein formulation by syringe or needle, for example.

Example 4

Osmolality, Viscosity and Density of Various Protein Formulations of the Invention Experiments were performed to measure the osmolality, viscosity and density of formulations according to the invention. The osmolality and viscosity data were generated from one specific lot of the anti-CCR5, humanized, monoclonal antibody PRO 140, while the density data were generated from two different lots of the same antibody. It was observed that the changes in osmolality and density were minor, i.e., approximately 20% in osmolality and less than about 5% in density, over the broad protein concentration range of 75 mg/mL to 225 mg/mL. The osmolalities ranged from 222 mOs/kg to 265 mOs/kg, and the densities ranged from 1.02 g/mL to 1.06 g/mL. However, the effect of the various protein concentrations on viscosity was much larger. Viscosity ranged from about 2 cP to about 75 cP. The increase in protein concentration (i.e., from 75 to 225 mg/mL) resulted in a linear increase in osmolality and density of the test formulations, while an exponential increase in viscosity was observed.

The extrapolated density data at a given protein concentration was determined. It was determined that if the protein concentration was about 150 mg/mL, about 175 mg/mL, about 200 mg/mL, about 225 mg/mL, and about 250 mg/mL, then its density was extrapolated to be about 1.045 g/mL, about 1.052 g/mL, about 1.059 g/mL, about 1.065 g/mL, and about 1.072 g/mL respectively.

Example 5

Subcutaneous Administration of PRO 140 in a Low Viscosity Formulation of the Invention A clinical study involving the subcutaneous administration of a high concentration of the humanized monoclonal antibody PRO 140, which is directed against the CCR5 chemokine receptor, in a formulation of the invention is designed to assess various injection sites in normal healthy adult subjects. The study further assesses the parameter of self-administration of the formulation containing the antibody in high concentration by subjects enrolled in the study.

The study (PRO 140 1103) is designed to evaluate the safety and tolerability of PRO 140 as a subcutaneous (SC) injection using an autoinjector delivery device (Autoject®2), (Owen Mumford Ltd., UK). The study examines PRO 140 at a dose of 350 mg administered subcutaneously using the Autoject®2 device in the subject's abdomen, arm, or thigh in a total volume of 2 ml (two 1 ml injections). The Autoject®2 device permits the passive injection of 1 ml volume. Subjects administer the final one or two injections during the second of two dosing days, following education procedures surrounding self-administration. Thus, the study further assesses a subject's ability to self administer the drug. Pharmacokinetic (PK) data evaluated from the study is used to ascertain the relative comparability of PRO 140 absorption following SC injection in the abdomen, arm, or thigh.

The 1103 study protocol is a single-center, open label clinical study in approximately 15 normal, healthy, adult subjects. Blood samples are obtained at screening to determine whether subjects meet the inclusion/exclusion criteria and include serologies, hematologies, comprehensive chemistry and metabolic profiles, urinalysis and urine drug screens. On Day 1 (Visit 2) subjects receive a total of 350 mg (2.0 ml) as two injections. Both injections are administered by the Principal Investigator or designee. The first injection of 1.0 ml is administered using the Autoject®2 in the abdomen, thigh, or arm. The second injection of 1.0 ml is also administered using the Autoject®2 on the contralateral side of the abdomen, thigh, or arm (depending on where the first injection was administered). On Day 8 (Visit 6), subjects receive a total of 350 mg (2.0 ml) as two injections. Both injections are administered by the Principal Investigator or designee. The first injection of 1.0 ml is administered using the Autoject®2 in the abdomen, thigh, or arm. The second injection of 1.0 ml is also administered using the Autoject®2 on the contralateral side of the abdomen, thigh, or arm (depending on where the first injection was administered). The administration of drug on Day 8 (Visit 6) differs from that on Day 1 (Visit 2) in that the Principal Investigator or designee administers the first injection and the subject self-administers the second injection. It will be understood that, as an alternative, the protocol could allow that the Principal Investigator or designee administers both the first and second injections. Safety, as assessed by adverse events (AEs), injection site reactions (ISRs) and vital signs, are monitored throughout the course of the study. Blood samples are also obtained for drug concentration data during study days 1, 2, 3, 5 and 8 (visits 2, 3, 4, 5 and 6, respectively).

The study comprises three phases, namely, a screening phase (up to fourteen days in duration), a treatment phase (fourteen days in duration) and an end of study phase (1 day in duration). In the screening phase, up to fourteen days prior to dosing and upon receipt of their signed and dated written informed consent, subjects have their eligibility status assessed prior to participation in the study. Subjects who meet all inclusion and exclusion criteria are enrolled in the study and are monitored throughout the study. At the end of study phase, subjects who have completed the treatment phase return to the site seven days later for the end of study phase assessments.

A formulation comprising a high concentration (175 mg/ml) of the humanized monoclonal antibody PRO 140 is parenterally administered. The route of administration is subcutaneous; an autoinjector device, i.e., the Autoject®2, is used; and injection is performed either in the arm, abdomen, or thigh of the subject using a 27 g needle. Fifteen subjects are randomly assigned in a 1:1:1 ratio to receive injections in the abdomen, arm, or thigh. A summary of the treatment therapy, dosage form, dosage regimen and mode of administration is provided in the below Table:

Treatment Therapy, Dosage Form, Regimen and Mode of Administration

| Study Drug and Visit | Dosage Form | PRO 140 Concentration | Injection Site | Dosing Frequency and Amount | Route of Administration |
|---|---|---|---|---|---|
| First Dose: Day 1 (Visit 2) PRO 140 | Parenteral Solution | 175 mg/mL | Abdomen, Arm or Thigh | Two injections: 1.0 mL Autoject® 2 and 1.0 mL Autoject® 2 | SC |
| Second Dose: Day 8 (Visit 6) PRO 140 | Parenteral Solution | 175 mg/mL | Abdomen, Arm or Thigh | Two injections: 1.0 mL Autoject® 2 and 1.0 mL Autoject® 2 | SC |

The study drug is administered on opposite sides of the abdomen, on opposite arms, or on opposite thighs. Following each SC delivery of drug, careful examinations of opposite arms are made to assess if any ISRs occur. Each dose of study drug is administered by SC injection sequentially using two syringes. Five subjects are randomly assigned to receive their injections in the abdomen; five subjects are randomly assigned to receive their injections in the arm; and five subjects are randomly assigned to receive their injections in the thigh. For both the abdominal and thigh sites of injection, the second injection is administered on the side contralateral to the site used for the first injection.

The first dose is administered to subjects on Day 1, Visit 2 in a total of 350 mg (total volume 2.0 ml), as two separate 1 ml injections using the Autoject®2. The first injection (syringe containing 1.0 ml) is administered in the abdomen, arm, or thigh by the Principal Investigator or designee. The second injection (syringe containing 1.0 ml) is administered on the contralateral side of the site of initial administration by the Principal Investigator or designee. The second dose is administered to subjects on Day 8 (Visit 6) and consists of a 350 mg dose (total volume 2.0 ml) administered as two separate 1.0 ml injections using the Autoject®2. The first injection (syringe containing 1.0 ml) is administered in the abdomen, arm, or thigh by the Principal Investigator or designee.

The second injection (syringe containing 1.0 ml) is administered on the contralateral side of the site of initial administration by the subject.

Example 6

Subcutaneous Administration of PRO 140 in a Low Viscosity Formulation of the Invention is Well-Tolerated A clinical study following the protocol described in Example 5 was conducted, with an exception that on Day 8, Visit 6, the second dose of study drug was not administered by the subject (i.e., no self-injection), but instead was administered via injection by the Principal Investigator or designee. The completion of such a clinical study indicated that subcutaneous delivery of PRO 140 via the Autoject®2 device was successful in all participating subjects. There were no reports of significant adverse effects resulting from administration of a high concentration of the humanized monoclonal antibody PRO 140, demonstrating the safety and tolerability of the high concentration PRO 140 formulation.

The contents of all patents, patent applications, published articles, books, reference manuals and abstracts as cited herein are hereby incorporated by reference in their entireties to more fully describe the state of the art to which the disclosure pertains. The citation of any patents, patent applications, published articles, books, reference manuals and abstracts, etc. cited herein is not intended to be an admission that they are indeed prior art.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variations that fall within the scope of the appended claims.

What is claimed is:

1. A formulation comprising concentrated PRO 140 in an amount greater than about 100 mg/mL and less than about 200 mg/mL; a tonicifier consisting essentially of a sodium salt and a histidine and glycine buffer present in a combined amount of from about 110 mM to about 120 mM and wherein the buffer is present in an amount of about 10 mM to about 25 mM; and a surfactant, wherein the formulation is hypotonic and has a total salt concentration of less than 100 mM.

2. The formulation of claim 1, wherein the salt is present in an amount of about 90 mM or about 95 mM.

3. The formulation of claim 1, wherein the salt is selected from sodium acetate, sodium chloride, sodium gluconate, sodium lactate, sodium thiocyanate, or a combination thereof.

4. The formulation of claim 1, wherein the surfactant is present in an amount between 0.001% w/v and 0.2% w/v.

5. The formulation of claim 1, wherein the surfactant is selected from a detergent, a pluronic, block copolymers, a polysorbate, polysorbate 20, polysorbate 80, a polyethylene glycol, or a combination thereof.

6. The formulation of claim 1, further comprising a stabilizing agent or a non-salt tonicifier present in an amount between 0.05% w/v and 1.8% w/v of the total formulation.

7. The formulation of claim 6, wherein the stabilizing agent or non-salt tonicifier is selected from a sugar alcohol, a monosaccharide, a disaccharide, sorbitol, mannitol, sucrose, trehalose, glycerol, maltose, lactose, or a combination thereof.

8. The formulation of claim 1, wherein the formulation has one or more of (a) a viscosity selected from about 25 cps to about 60 cps; (b) a pH of from about 5.4 to about 6.4; or (c) an osmolality of less than about 290 mOs/kg.

9. The formulation of claim 1, wherein the formulation comprises a therapeutic protein for subcutaneous administration to a subject in need thereof; wherein the therapeutic protein is administered via a syringe, a pen, a pump, a cartridge, a two-chambered cartridge, a multishot needle syringe, a multidose needle syringe, a multidose pen, a jet injector, a syrette, an autoinjector, or a pre-filled syringe; and wherein the formulation is in liquid or solution form.

10. A formulation comprising:
concentrated PRO 140 in an amount greater than about 100 mg/mL and less than about 200 mg/mL;
a sodium salt in an amount greater than about 90 mM and less than 100 mM;
a histidine and glycine buffer in an amount greater than about 5 mM and less than about 25 mM;
a surfactant in an amount greater than about 0.001% w/v and less than about 0.2% w/v; and, optionally,
a stabilizing agent or non-salt tonicifier in an amount of about 0.05% w/v to about 1.8% w/v;
wherein the formulation has an osmolality of about 250 to about 280 mOsm and has a total salt concentration of less than 100 mM.

11. A low viscosity, hypotonic formulation, comprising:
(a) concentrated PRO 140 in an amount greater than about 100 mg/mL and less than about 200 mg/mL;
(b) a sodium salt in an amount selected from about 90 mM or about 95 mM;
(c) a histidine and glycine buffer in an amount of about 20 mM;
(d) a surfactant in an amount of 0.005% to 0.2% w/v; and optionally
(e) a stabilizing agent or non-salt tonicifier in an amount sufficient to provide an osmolality of the formulation of about 260-280 mOs/kg;
wherein the formulation has a total salt concentration of less than 100 mM.

12. A low viscosity hypotonic formulation, comprising:
(a) concentrated PRO 140 in an amount greater than about 100 mg/mL and less than about 200 mg/mL;
(b) a salt in an amount selected from about 90 mM or about 95 mM, wherein the salt is selected from sodium chloride, sodium gluconate, or sodium lactate;
(c) a histidine and glycine buffer in an amount of about 20 mM;
(d) a surfactant in an amount of about 0.005% to about 0.2% w/v, wherein the surfactant is a polysorbate, a poloxamer, or a pluronic; and
(e) a stabilizing agent or non-salt tonicifier present in an amount sufficient to provide an osmolality of the formulation of about 230 mOs/kg to about 280 mOs/kg, wherein the stabilizing agent or non-salt tonicifier is selected from a sugar alcohol, a monosaccharide, a disaccharide, or a combination thereof;
wherein the formulation has a total salt concentration of less than 100 mM.

13. A composition comprising PRO 140 in an amount greater than about 100 mg/mL and less than about 200 mg/mL, a tonicifier comprising a sodium salt present in a concentration of greater than about 90 mM and a histidine and glycine buffer present in a combined amount of from 110 mM to 120 mM and a surfactant present in an amount of from about 0.001% to about 0.2% w/v, wherein the composition has an osmolality of about 230 to about 290 mOs/kg and a total salt concentration of less than 100 mM.

14. The composition of claim 13, wherein (a) the PRO 140 is present in an amount of 120 mg/mL to 185 m/mL; (b) the salt is present in an amount of 90 mM or in an amount of 95 mM and is selected from one or more of sodium chloride, sodium gluconate, or sodium lactate; (c) the buffer is present in an amount of 20 mM; and (d) the surfactant is present in an amount of 0.005% w/v and is selected from one or more of a polysorbate, polysorbate 20, polysorbate 80, or a pluronic.

15. The composition of claim 13, further comprising a non-salt tonicifier in an amount of from 0.05% to 1.5% w/v and selected from one or more of sorbitol, mannitol, sucrose, trehalose, or glycerol.

16. The composition of claim 13, further wherein the composition has a pH of about 5.4 to 5.6 and suitability for subcutaneous administration.

17. An article of manufacture comprising a container and a formulation comprising PRO 140 in a concentration of greater than 100 mg/mL and less than 200 mg/mL, a tonicifier of a sodium salt present in a concentration of greater than about 90 mM and a histidine and glycine buffer present in a combined amount of from about 110 mM to about 120 mM and the formulation has a total salt concentration of less than 100 mM, a surfactant in an amount of from about 0.005% to about 0.2%, and instructions for use.

18. The article of manufacture of claim 17, wherein the container is selected from a bottle, a vial, a syringe, a pen, a pump, a multidose needle syringe, a multidose pen, a jet injector, a syrette, an autoinjector, a pre-filled syringe, or a combination thereof.

19. The article of manufacture of claim 17, wherein the formulation is included in the container.

20. The formulation of claim 11, wherein the formulation has a viscosity from about 15 cps to about 40 cps.

21. The formulation of claim 1, wherein the formulation has a viscosity from about 15 cps to about 40 cps.

* * * * *